(12) United States Patent
Clark et al.

(10) Patent No.: US 7,597,010 B1
(45) Date of Patent: Oct. 6, 2009

(54) METHOD OF ACHIEVING HIGH TRANSDUCTION UNDER TENSION OR COMPRESSION

(75) Inventors: Arthur E. Clark, Adelphi, MD (US); Marilyn Wun-Fogle, Potomac, MD (US); James B. Restorff, College Park, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 135 days.

(21) Appl. No.: 11/274,635

(22) Filed: Nov. 15, 2005

(51) Int. Cl.
    *G01L 3/00* (2006.01)
(52) U.S. Cl. .................................. 73/862.335
(58) Field of Classification Search ............................... 73/862.331–862.338
    See application file for complete search history.

(56) References Cited

U.S. PATENT DOCUMENTS

| | | | | |
|---|---|---|---|---|
| 3,336,154 A | * | 8/1967 | Oberg et al. | 427/8 |
| 3,638,153 A | * | 1/1972 | Sparrow | 335/215 |
| 3,774,134 A | * | 11/1973 | Kardashian et al. | 336/20 |
| 3,833,431 A | * | 9/1974 | Foster et al. | 148/113 |
| 3,892,118 A | * | 7/1975 | Wiegand | 72/371 |
| 3,961,297 A | * | 6/1976 | Garshelis | 335/3 |
| 4,053,333 A | * | 10/1977 | Egami et al. | 148/120 |
| 4,748,000 A | | 5/1988 | Hayashi et al. | |
| 4,894,615 A | * | 1/1990 | Mermelstein | 324/244 |
| 4,904,543 A | | 2/1990 | Sakakima et al. | |
| 5,305,075 A | * | 4/1994 | Bucholtz et al. | 356/477 |
| 5,449,418 A | * | 9/1995 | Takagi et al. | 148/304 |
| 5,493,921 A | | 2/1996 | Alasafi et al. | |
| 5,600,329 A | * | 2/1997 | Brenner | 342/357.03 |
| 5,706,572 A | * | 1/1998 | Garshelis | 29/602.1 |
| 5,958,153 A | | 9/1999 | O'Handley et al. | |
| 5,993,565 A | * | 11/1999 | Pinkerton et al. | 148/104 |
| 6,139,648 A | * | 10/2000 | Wun-Fogle et al. | 148/121 |
| 6,176,943 B1 | * | 1/2001 | Wun-Fogle et al. | 148/108 |

(Continued)

OTHER PUBLICATIONS

Cullen, J.R., Clark, A.E., Wun-Fogle, M., Restorff, J.B., and Lograsso, T.A., "Magnetoelasticity of Fe-Ga and Fe-Al Alloys", Journal of Magnetism and Magnetic Materials 226-230(2001) 948-949.

(Continued)

*Primary Examiner*—Lisa M Caputo
*Assistant Examiner*—Octavia Davis
(74) *Attorney, Agent, or Firm*—Jane Barrow; Dave A. Ghatt

(57) ABSTRACT

A method of using a magnetostrictive material to achieve a high magnetomechanical coupling factor comprising building an internal anisotropy energy into the magnetostrictive material and applying a tensile or compressive stress to the magnetostrictive material with the built-in internal anisotropy energy. The internal anisotropy energy is built into the magnetostrictive material by annealing the magnetostrictive material under an annealing stress or a suitable magnetic field. For a positive magnetostrictive material, when the annealing stress is compressive, the stress applied to the annealed material under operation is tensile, and when the annealing stress is the tensile, the stress applied to the annealed material under operation is compressive. For a negative magnetostrictive material, when the annealing stress is compressive, the stress applied to the annealed material under operation is tensile, and when the annealing stress is tensile, the stress applied to the annealed material under operation is compressive.

8 Claims, 3 Drawing Sheets

STRESS ANNEALING FURNACE

U.S. PATENT DOCUMENTS 6,254,695 B1 * 7/2001 Herzer et al. ............... 148/108
6,352,649 B1 * 3/2002 McCallum et al. ........ 252/62.55
6,595,073 B1 * 7/2003 Yagi et al. .............. 73/862.333

OTHER PUBLICATIONS

Clark, A.E., Wun-Fogle, M., Restorff, J.B., Lograsso, T.A. and Petculescu, G. "Magnetostriction and Elasticity of b.c.c. Fe100-xBex Alloys", 9th Joint MMM-Intermag Conference, Jan. 5-9, 2004, Abstract Designation EC-03.

N. Srisukhumbowornchai and S. Guruswamy, "Large Magnetostrictive in Directionally Solidified FeGa and FeGaAl Alloys", J. Appl. Phys., vol. 90, No. 11 Dec. 1, 2001, pp. 5680-5688. (Accepted Aug. 25, 2001 Published Dec. 2001).

Kawamiya, Nobuo, Adachi, Kengo and Nakamura, Yoji, Journal of the Physical Society of Japan., vol. 33, No. 5, Nov. 1972 pp. 1318-1327.

Kellogg, R.A., Flatau, A.B., Clark, A.E., Wun-Fogle, M. and Lograsso, T.A., "Temperature and Stress Dependencies of the Magnetic and Magnetostrictive Properties of Fe0.81Ga.19", Journal of Applied Physics, vol. 11, No. 10, May 15, 2002, pp. 7821-7823.

Clark, Arthur E., Wun-Fogle, Marilyn, Restorff, James B. and Lograsso, Thomas A., "Magnetostrictive Properties of Galfenol Alloys Under Compressive Stress", Materials Transactions, vol. 43, No. 5 (2002) pp. 881-886.

Restorff, J.B., Wun-Fogle, M., Clark, A.E., Lograsso, T.A., Ross, A.R. and Schlagel, D.L., "Magnetostriction of Ternary Fe-Ga-X Alloys (X=Ni,Mo,Sn,Al)", Journal of Applied Physics, vol. 91, No. 10, May 15, 2002, pp. 8225-8227.

Guruswamy, S, Srisukhumbowornchai, N., Clark, A.E., Restorff, J.B., And Wun-Fogle, M., "Strong, Ductile, and Low-Field-Magnetostrictive Alloys Based On Fe-Ga", Scripta Mater, 43, (2002) pp. 239-244.

Clark, A.E., Restorff, J.B., Wun-Fogle, M. and Lograsso, T.A. "Magnetostriction Properties of Fe-Ga Alloys Under Large Compressive Stresses", The 2000 IEEE International Magnetics Conference, Digest Intermag 2000, BS-12, Apr. 8, 2000 2 pages.

Clark, A.E., Wun-Fogle, M., Restorff, J.B., Lograsso, T.A. and Schlagel, D.L., Magnetostrictive Galfeno/Alfenol Single Crystal Alloys Under Large Compressive Stresses, Actuator 2000, 7th International Conference On New Actuators, Jun. 18, 2000, pp. 111-115.

H. Okamoto, Phase Diagrams of Binary Iron Alloys, ASM International, Materials Park, OH, pp. 147-151.

H. Okamoto and L.E. Tanner, "Phase Diagrams of Binary Beryllium Alloys", ASM International Metals Park, Ohio, pp. 81-96.

Cheng, S.F., Das, B.N., Wun-Fogle, M, Lubitz, P., and Clark, A.E., "Structure of Melt-Spin Fe-Ga Based Magnetostrictive Alloys", Paper # AE06, Intermag Europe 2002, Apr. 28-May 2, 2002 Amsterdam, The Netherlands, pp. 1-3.

Lograsso, T.A., Ross, A.R., Schlagel, D.L., Clark, A.E., Wun-Fogle, M.., "Structural Transformations in Quenched Fe-Ga Alloys", Journal of Alloys and Compounds 350 (2003) pp. 95-101.

Clark, A.E., Hathaway, K.B., Wun-Fogle, M., Restorff, J.B., Lograsso, T.A., Keppens, V.M., Petculescu, G. and Taylor, R.A., "Extraordinary Magnetoelasticity and Lattice Softening in bcc Fe-Ga Alloys", Journal of Applied Physics, vol. 93, No. 10, May 15, 2003, pp. 8621-8623.

Kellogg, R.A., Flatau, A.B., Clark A.E, Wun-Fogle, M., and Lograsso, T.A. "Texture and Grain Morphology Dependencies of Saturation Magnetostriction in Rolled Polycrystalline Fe83Ga17", Journal of Applied Physics, vol. 93, No. 10, May 15, 2003. pp. 8495-8497.

Restorff, J.B., Wun-Fogle, M., Clark, A.E., Lograsso, T.A., Ross, A.R. and Schlagel, D.L., "Magnetostriction and Magnetization of Ternary Fe-Ga-X Alloys (X=Sn,Ni,Mo)", Abstracts, 46th Conference on Magnetism & Magnetic Materials, Seattle, Washington, Nov. 12-16, 2001, pp. 274-275.

Clark, Arthur E., Restorff, James B., Wun-Fogle, Marilyn, Lograsso, Thomas A. and Schlagel, Deborah L., "Magnetostrictive Properties of b.c.c. Fe-Ga and Fe-Ga-Al Single Crystals", Poster Presentation, Intermag 2000, Apr. 10, 2000, 17 pages.

Clark, Arthur E., Restorff, James B., Wun-Fogle, Marilyn, Lograsso,Thomas A. and Schlagel, Deborah L., "Magnetostrictive Properties of Body-Centered Cubic Fe-Ga and Fe-Ga-al Alloys", IEEE Transactions on Magnetics, vol, 36, No. 5, Sep. 2000, pp. 3238-3240.

Kellogg. R.A., Russell, A.M., Lograsso, T.A., Flatau, A.B.,Clark, A.E. and Wun-Fogle, M., "Mechanical Properties of Magnetostrictive Iron-Gallium Alloys", SPIE's 10th Annual International Symposium on Smart Structures and Materials, Mar. 2-6, 2003, paper#5053-70.

Clark, Arthur E., Wun-Fogle, Marilyn, Restorff, James B., Lograsso, Thomas A. and Schlagel, Deborah L., "Magnetostricive Alfenol/ Galfenol Alloys Under Large Compressive Stresses", Presentation, Actuator 2000, Jun. 19-21, 2000, 17 pages.

Clark, Arthur E, Wun-Fogle, Marilyn, Restorff, James B., Lograsso, Thomas A. and Cullen, James R., "Effect of Quenching on The Magnetostriction of Fe1-xGax(0.13 < x < 0.21)", IEEE Transactions on Magnetics, vol. 37 No. 4, Jul. 2001, pp. 2678-2680.

Clark, Arthur E., Wun-Fogle, Marilyn, Restorff, James B., Lograsso, Thomas A., Ross, Amy R. and Cullen, James R., "Effect of Quenching on the Magnetostriction of Fe1-xGax", The 8th Joint MMM-Intermag Conference, Jan. 7, 2001, p. 284.

Clark, Arthur E, Wun-Fogle, Marilyn, Restorff, James B., Lograsso, Thomas A., Ross, Amy R. and Cullen, James R., "Effect of Quenching on the Magnetostriction of Fe1-xGax", The 8th Joint MMM-Intermag Conference, Presentation, Jan. 7-11, 2001, 15 pages.

Gersdorf, Robert, "On Magnetostriction of Single Crystals of Iron and Some Dilute Iron Alloys", PhD. Thesis, Universiteit van Amsterdam, Nov. 22, 1961.

Kellogg, Rick A., Flatau, Alison, Clark, Arthur E., Wun-Fogle, Marilyn and Lograsso, Thomas, "Quasi-Static Transduction Characterization of Galfenol", 2003 ASME International Mechanical Engineering Congress & Exposition. Nov. 16-21, 2003, Washington, D.C., pp. 1-8.

Viehland, D., Li, J.F. Lograsso, T.A., Ross, A., Wuttig, Manfred, "Structural Studies of Fe0.81Ga0.19 by reciprocal Space Mapping", Applied Physics Letters, vol. 81, No. 17, Oct. 21, 2002 pp. 3185-3187.

Dai, Liyang, Cullen, James, Wuttig, Manfred, Lograsso, T. Quandt, Eckhard, "Magnetism, Elasticity, and Magnetostriction of FeCoGa Alloys", Journal of Applied Physics, vol. 93, No. 10, May 15, 2003, pp. 8627-8629.

Lograsso, T.A., Schlagel, D.L., and Ross, A.R., "Influence of Crystal Chemistry on Magnetoelastic Properties in Fe-Ga A", Internet search, 3 pages.

Srisukhumbowornchai, N. and Guruswamy S., Abstract "Influence of Ordering on the Magnetostriction of Fe-27.5 at % Ga Alloys", Internet Search, 2 pages.

Kellogg, R.A., Flatau, A.B., Clark, A.E., Wun-Fogle; M. and Lograsso, T.A., Abstract "Texture and Grain Morphology Dependencies of Saturation Magnetostriction in Rolled Polycrystalline Fe83Ga17", Internet search, 2 pages.

Clark, Arthur E., Wun-Fogle, Marilyn, Restorff, James B., Lograsso, Thomas A. and Petculescu, Gabriella, "Magnetostriction and Elasticity of b.c.c. Fe100-xBex Alloys". Presentation, The 9th Joint MMM-Intermag Conference Jan. 5-9, 2004, 13 pages.

Office Action of Parent Case U.S. Appl. No. 10/182,095, date mailed Aug. 25, 2003, 12 pages.

PCT International Preliminary Examination Report, File Copy 409, PCT/US01/02795, 10 pages.

PCT International Search Report, File Copy 210, PCT/US01/02795, 7 pages.

Kellogg, Rick Allen, "Development and Modeling of Iron-Gallium Alloys", PhD. Thesis, Iowa State University, Ames, Iowa (2003).

Restorff, J.B., Wun-Fogle, M and Clark, A.E. "High Magnetomechanical Coupling Of Transduction Elements Under Tension", 11th CF/DRDC International Meeting on Naval Application of Materials Technology, Darmouth, Nova Scotia, Jun. 7-9, 2005 5 pages.

U.S. Appl. No. 11/053,753, filed Jan. 31, 2005, entitled "High Magnetostriction of Positive Magnetostrictive Materials under Tensile Load," joint inventors Arthur E. Clark, James B. Restorff and Marilyn Wun-Fogle.

International Application published under the Patent Cooperation Treaty (PCT), International Publication No. WO 01/55687 A2, International Application No. PCT/US01/02795, international filed date Jan. 29, 2001, title "Magnetostrictive Devices and Methods using High Magnetostriction, High Strength FeGa Alloys," joint inventors Arthur E. Clark et al.

* cited by examiner

STRESS ANNEALING FURNACE

Threaded sample

SCHEMATIC OF THE TENSILE STRESS MEASUREMENT APPARATUS

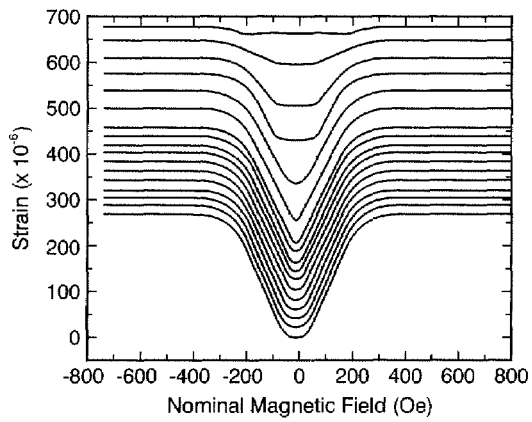
FIG. 3 A Typical measurement set showing the magnetostriction at tensile stresses from 0.2 to 30 MPa. The lowest stresses are at the bottom.
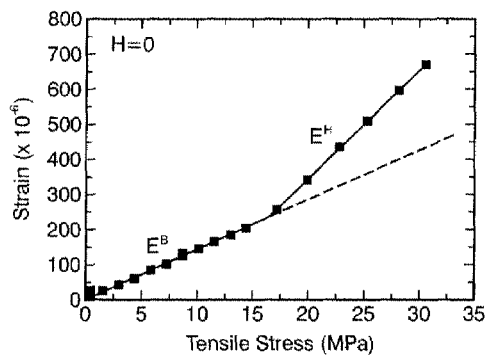
FIG. 4A $E^H$=32.8 GPa; $E^B$=74.5 GPa; $k$=0.75 (Sample 1174A)
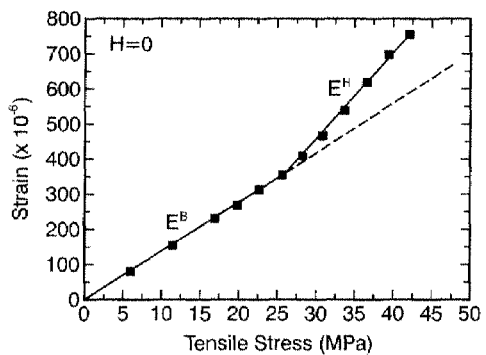
FIG. 4B $E^H$=36.3 GPa; $E^B$=73.7 GPa; $k$=0.71 (Sample 1184AA)
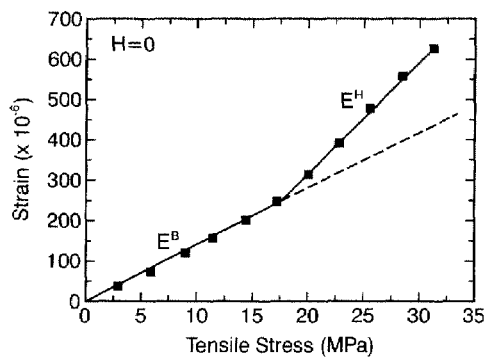
FIG. 4C $E^H$=33.4 GPa; $E^B$=73.3 GPa; $k$=0.74 (Sample 1177AA)
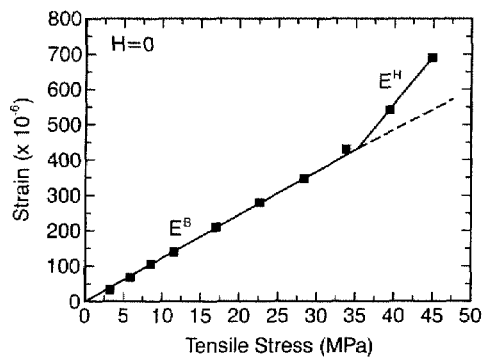
FIG. 4D $E^H$=35.9 GPa; $E^B$=81.2 GPa; $k$=0.75 (Sample 1199AE)

METHOD OF ACHIEVING HIGH TRANSDUCTION UNDER TENSION OR COMPRESSION

STATEMENT OF GOVERNMENT INTEREST

The invention described herein may be manufactured and used by or for the Government of the United States of America for governmental purposes without the payment of any royalties thereon or therefor.

BACKGROUND

1. Field of the Invention The present invention relates to transduction, and, more specifically, to a method of using a magnetostrictive material to achieve high transduction under compression or tension.

2. Description of the Prior Art

Magnetostriction refers to a change in dimensions, often the length, of a magnetic material with a change in its magnetic state. Often, the change in magnetic state results from the application of a magnetic field. By definition, a positive magnetic material expands in the direction of the field upon application of a magnetic field, and a negative material contracts upon application of a field. Alternatively, a change in dimensions of a magnetostrictive material can cause a change in magnetization and thus produce an emf in an adjoining coil. Therefore, a positive or negative magnetostrictive material can act as a transducer or motor, converting between electrical and mechanical energy (or work).

Magnetostrictive materials are commonly operated with a compressive load condition and can sometimes also operate under a tensile load condition. Typically, positive magnetostrictive materials are operated under compression. Likewise, negative materials work optimally under tension. Note that many of the high power active materials available today are brittle and cannot withstand any substantial amount of tensile stress.

Many of the currently available magnetostrictive materials have only nominal magnetomechanical coupling factors (k). (The square of the coupling factor ($k^2$), which is a measure of transduction, is defined as the fraction of the total energy that is transformed from the magnetic state to the mechanical state. Perfect transduction occurs when k equals 1.) For example, nickel has a coupling factor of only about 0.3, indicating only about a 10% transformation from the magnetic state to the mechanical state. Therefore, most magnetostrictive materials achieve low transduction, which affects the efficiency and performance of the transduction device.

SUMMARY

The aforementioned problems with the current technologies are overcome by the present invention wherein high transduction is achieved in magnetostrictive materials by building an internal anisotropy energy into the magnetostrictive material and applying a tensile or compressive stress to the magnetostrictive material with the built-in internal anisotropy energy. The internal anisotropy energy is built into the magnetostrictive material by annealing the magnetostrictive material under an annealing stress or a suitable magnetic field. For a positive magnetostrictive material, when the annealing stress is compressive, the stress applied to the annealed material under operation is tensile, and when the annealing stress is tensile, the stress applied to the annealed material under operation is compressive. For a negative magnetostrictive material, when the annealing stress is compressive, the stress applied to the annealed material under operation is tensile, and when the annealing stress is tensile, the stress applied to the annealed material under operation is compressive.

The present invention is useful for providing highly efficient transduction devices, actuators, and positioners. Possible uses include sonar projectors and sensors, stepping motors, noise cancellation devices, vibration mounts, structure realignment devices, and ultrasonic cleaners.

BRIEF DESCRIPTION OF THE DRAWINGS

These and other features and advantages of the invention, as well as the invention itself, will become better understood by reference to the following detailed description, appended claims, and accompanying drawings where:

FIG. 3 is a typical measurement set showing the magnetostriction at tensile stresses from 0.2 to 30 MPa (the lowest stresses are at the bottom);

FIG. 4(a) is a stress-strain curve when $E^H$=32.8 GPa, $E^B$=74.5 GPa, and k=0.75;

FIG. 4(b) is a stress-strain curve when $E^H$=36.3 GPa, $E^B$=73.7 GPa, and k=0.71;

FIG. 4(c) is a stress-strain curve when $E^H$=3.34 GPa, $E^B$=73.3 GPa, and k=0.74; and FIG. 4(d) is a stress-strain curve when $E^H$=35.9 GPa, $E^B$=81.2 GPa, and k=0.75.

DETAILED DESCRIPTION

In a preferred embodiment, a magnetostrictive material is annealed under stress (and/or magnetic fields) to build in an internal anisotropy energy ($E_k$), a stress is applied to the annealed material, and under operation a second magnetic field is applied to convert the internal anisotropy energy into useful work or to reconvert the external work into the original internal anisotropy energy.

The internal anisotropy energy can be built into the magnetostrictive material by annealing the material under stress and/or annealing while applying a suitable magnetic field. When this internal energy equals the external stress energy during operation, the conversion between $E_k$ and the external work ($\lambda \times \sigma$) requires only a small magnetic energy ($\lambda$ is the saturation magnetostriction, and $\sigma$ is the externally applied stress). Thus, in a preferred embodiment, high transduction is achieved by using a magnetostriction material with $E_k$, under a stress of $\sigma = E_k/\lambda$. At this stress, a small triggering magnetic energy can convert the internal energy introduced by the stress anisotropy into useful work, or conversely it can reconvert the external work into the original internal stored energy. This follows from energy minimization of the simple magnetization rotation model. For simplification, the model assumes that the material is homogeneous and that there is a single value of built-in $E_k$. The equation for this model is shown in Equation 1 where k is the coupling factor, $s_m$ is the compliance, $M_s$ is the magnetization, and H is the magnetic field.

$$k^2 = [1 + s_m(E_k - \lambda\sigma)^3/18\lambda^2 M_s^2 H^2)]^{-1/2} \quad (1)$$

Since $s_m$, $\lambda$, and $M_s$ are not vanishing, this expression shows that for any field H ($\neq 0$) when $E_k = \lambda \times \sigma$, the coupling factor k equals unity, i.e., perfect magnetomechanical transduction. Obviously, all materials have some inhomogenities and impurities that lead to somewhat lower coupling factors. For example, the stress annealing process may result in a distribution of $E_k$'s.

For a positive magnetostrictive material operated under compression, σ is negative; therefore, $E_k$ must be negative and built-in with a tensile load or a suitable magnetic field. Optimum operation is at a compressive stress of $\sigma = E_k/\lambda$. High coupling could even occur under a very high compressive load, the limit of the load being subjected to the limit of the built-in $E_k$.

For a negative magnetostrictive material (such as nickel or a nickel alloy) operated under compression, $E_k$ is built-in by annealing under a tensile stress or a suitable magnetic field.

For a positive magnetostrictive material operated under tension, $E_k$ is built-in under compression or a suitable magnetic field.

For a negative magnetostrictive material operated under tension, $E_k$ is built-in under compression or a suitable magnetic field.

Experiment

Figure 1:
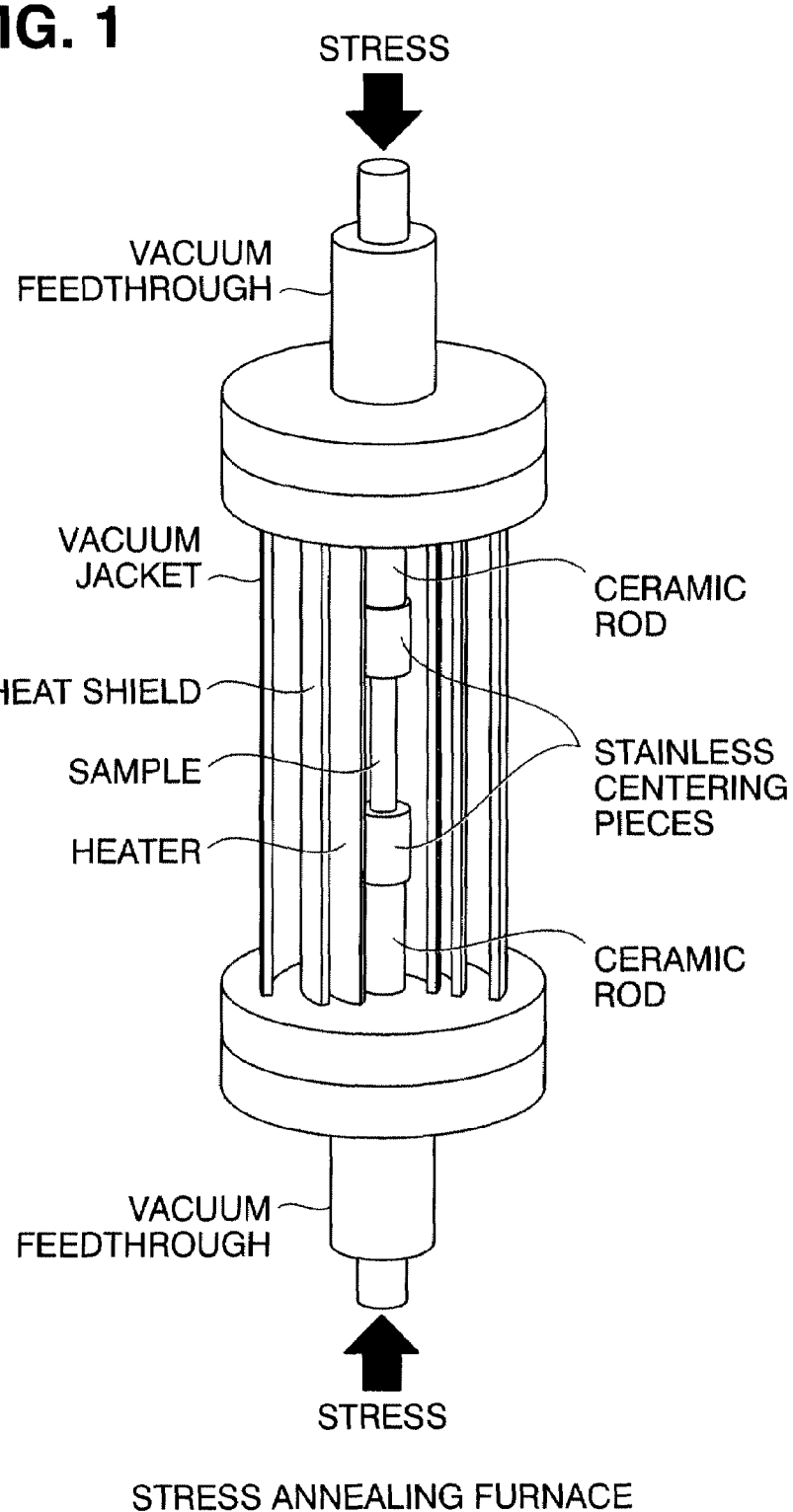
FIG. 1 shows a stress annealing furnace.

Highly textured $Fe_{81.6}Ga_{18.4}$ rods 6.35 mm diameter ×50.8 mm long (0.25×2.00 in) were annealed under (compressive) stresses of between −100 and −219 MPa at 600° C. for 20 minutes using the furnace shown in FIG. 1. The furnace consists of an outer vacuum jacket, a stainless steel heat shield and a Nichrome heater wound on a ceramic form. Stress was applied by a hand-operated hydraulic pump via two alumina rods. Stainless steel centering rings kept the sample in place on the alumina rods. Only a moderate (~200 micron) vacuum was used. Further details can be found in M. Wun-Fogle, J. B. Restorff, Kitty Leung, and A. E. Clark, "Magnetostriction of Terfenol-D Heat Treated Under Compressive Stress," IEEE Transactions on Magnetics, 35, 3817-3819 (1999), the entire contents of which are incorporated herein by reference.

Figure 2:
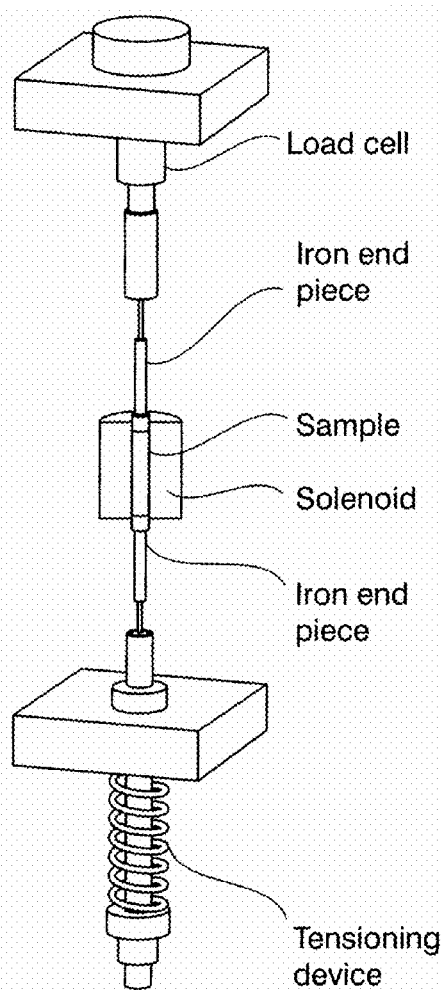
FIG. 2 is a schematic of the tensile stress measurement apparatus.
Figure 2:
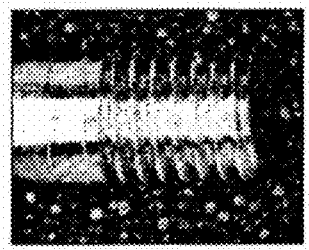

The magnetostriction was measured under tensile stress using the apparatus shown in FIG. 2. Soft iron end-pieces, 6.35×31.8 mm, were attached to the sample using ¼-28 threads that were machined into the samples (see inset of FIG. 2). Two 4-40 stainless steel threaded rods about 25.4 mm long were used in the load path; the rods were flexible enough to allow for some small amount of misalignment. Stress was applied via a spring indicated by the tensioning device shown in FIG. 2. Measurements were started near 0.3 MPa and stopped when the magnetostrictions dropped to about 30 percent of their starting values which usually occurred between 40 and 50 MPa. The magnetic field was supplied by a water-cooled, temperature controlled coil which also stabilized the temperature of the samples. Strains were measured by two Vishay Micro-Measurements WK-06-500GB-350 strain gages mounted on opposite sides of the Galfenol rods; the average of the two strain gages was used. A typical measurement set is shown in FIG. 3. At each applied stress, the zero field value of the strain was measured and the resulting stress-strain curve was plotted. Four samples are shown in FIGS. 4(a)-4(d). The moduli were determined by fitting the hard and soft modulus regions to a straight line. The coupling coefficient k was determined by Equation 2 where $E^H$ is the soft modulus and $E^B$ is the hard modulus.

$$k = [1 - (E^H/E^B)]^{1/2} \quad (2)$$

Thirteen measurements on eleven samples were made (two were annealed twice). Table 1 shows the results of all samples. The annealing conditions, $E^H$, $E^B$, and k are also shown. Five of the thirteen measurements showed k≧0.7. Average values of the hard and soft modulus were $E^H$=40±7 and $E^B$=72±7. The average value of k was 0.66±0.08.

TABLE 1

Annealing conditions, moduli and k.
The "A" after the sample number indicates annealed, and multiple "A"s reflect multiple anneals.

| | Annealing Parameters | | | | | |
|---|---|---|---|---|---|---|
| Sample # | Stress (MPa) | Temp (° C.) | Time (min) | $E^B$ (GPa) | $E^H$ (GPa) | k |
| 1173A | 100 | 625 | 10 | 59.4 | 41.9 | 0.54 |
| 1174A | 100 | 625 | 10 | 74.5 | 32.8 | 0.75 |
| 1175A | 100 | 600 | 20 | 62.2 | 33.3 | 0.68 |
| 1176A | 200 | 600 | 20 | 74.6 | 40.9 | 0.67 |
| 1177AA | 100 | 635 | 20 | 73.3 | 33.4 | 0.74 |
| 1177AAA | 150 | 635 | 20 | 75.6 | 40.6 | 0.68 |
| 1178A | 100 | 635 | 100 | 77.1 | 53.0 | 0.56 |
| 1181A | 200 | 600 | 20 | 78.0 | 42.6 | 0.67 |
| 1183A | 200 | 600 | 20 | 71.1 | 48.6 | 0.56 |
| 1184AA | 150 | 600 | 20 | 73.7 | 36.3 | 0.71 |
| 1198A | 200 | 600 | 20 | 68.2 | 40.8 | 0.63 |
| 1199A | 200 | 600 | 20 | 79.6 | 40.5 | 0.70 |
| 1199AE | 1199A Magnetic Field Cycled | | | 81.2 | 35.9 | 0.75 |

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g., using the articles "a," "an," "the," or "said" is not construed as limiting the element to the singular.

What is claimed is:

1. A method of using a magnetostrictive material having built-in anisotropy energy to achieve a high magnetomechanical transduction comprising:

applying an operational tensile or compressive stress to said magnetostrictive material having said built-in anisotropy energy such that said operational tensile or compressive stress is about equal to said built-in anisotropy energy divided by a saturated magnetostriction of said magnetostrictive material;

applying a triggering magnetic field to said magnetostrictive material; and obtaining said high magnetomechanical transduction; and wherein said saturated magnetostriction is up to about 250 ppm;

wherein said magnetostrictive material is either a positive or negative magnetostrictive material, and wherein said magnetostrictive material is an alloy containing iron and gallium.

2. The method of claim 1, wherein said magnetostrictive material is positive and wherein when said positive magnetostrictive material is used to achieve said high magnetomechanical transduction, annealing compressive stress is used to form said built-in anisotropy energy in said positive magnetostrictive material, and wherein said operational tensile stress is applied to said positive magnetostrictive material having said built-in anisotropy energy by said annealing compressive stress.

3. The method of claim 2, wherein when said positive magnetostrictive material is used to achieve said high magnetomechanical transduction, annealing tensile stress is used to form said built-in anisotropy energy in said positive magnetostrictive material, and wherein said operational compressive stress is applied to said positive magnetostrictive material having said built-in anisotropy energy by said annealing tensile stress.

4. The method of claim 1, wherein said magnetostrictive material is negative and wherein when said negative magnetostrictive material is used to achieve said high magnetomechanical transduction, annealing compressive stress is used to form said built-in anisotropy energy in said negative magnetostrictive material, and wherein said operational tensile stress is applied to said negative magnetostrictive material having said built-in anisotropy energy by said annealing compressive stress.

5. The method of claim 4, wherein when said negative magnetostrictive material is used to achieve said high magnetomechanical transduction, said annealing tensile stress is used to form said built-in anisotropy energy in said negative magnetostrictive material, and wherein said operational compressive stress is applied to said negative magnetostrictive material having said built-in anisotropy energy by said tensile annealing stress.

6. The method of claim 1, wherein said magnetostrictive material is highly textured.

7. A method of using a positive magnetostrictive material having built-in anisotropy energy by annealing the material under an annealing stress and/or annealing while applying a magnetic field to achieve a high magnetomechanical transduction comprising:

applying an operational tensile stress to said positive magnetostrictive material having said built-in anisotropy energy such that said operational tensile stress is about equal to said built-in anisotropy energy divided by the saturated magnetostriction of said positive magnetostrictive material;

applying a triggering magnetic field to said positive magnetostrictive material; and obtaining said high magnetomechanical transduction; and wherein said built-in anisotropy energy is built into said positive magnetostrictive material by annealing said magnetostrictive material under an annealing compressive stress, wherein said saturated magnetostriction is up to about 250 ppm, and wherein said positive magnetostrictive material is an alloy containing iron and gallium.

8. A method of using a negative magnetostrictive material having built-in anisotropy energy by annealing the material under an annealing stress and/or annealing while applying a magnetic field to achieve a high magnetomechanical transduction comprising:

applying an operational compression stress to said negative magnetostrictive material having said built-in anisotropy energy such that said operational compression stress is about equal to said built-in anisotropy energy divided by the saturated magnetostriction of said negative magnetostrictive material;

applying a triggering magnetic field to said negative magnetostrictive material; and obtaining said high magnetomechanical transduction; and wherein said built-in anisotropy energy is built into said negative magnetostrictive material by annealing said magnetostrictive material under an annealing tensile stress, wherein said saturated magnetostriction is up to about 250 ppm, and wherein said magnetostrictive material is an alloy containing iron and gallium.

* * * * *